United States Patent [19]

Henrie, II et al.

[11] Patent Number: 5,639,753

[45] Date of Patent: Jun. 17, 1997

[54] INSECTICIDAL PTERIDINES AND 8-DEAZAPTERIDINES

[75] Inventors: Robert N. Henrie, II, East Windsor; Clinton J. Peake, Trenton; Thomas G. Cullen, Milltown; Albert C. Lew, Princeton Junction; Ian R. Silverman, Maple Shade, all of N.J.

[73] Assignee: FMC Corporation, Philadelphia, Pa.

[21] Appl. No.: 612,657

[22] Filed: Nov. 28, 1995

Related U.S. Application Data

[63] Continuation of Ser. No. 67,897, May 27, 1993, Pat. No. 5,521,190.

[51] Int. Cl.$^6$ .......................... A01N 43/54; A01N 43/60
[52] U.S. Cl. .......................... 514/249; 514/258; 514/260; 514/279
[58] Field of Search .......................... 514/249, 258; 544/200, 279

[56] References Cited

U.S. PATENT DOCUMENTS

| | | | |
|---|---|---|---|
| 4,425,346 | 1/1984 | Horlington | 514/258 |
| 4,820,706 | 4/1989 | Khaled et al. | 514/258 X |

FOREIGN PATENT DOCUMENTS 32652  7/1989  European Pat. Off. .

OTHER PUBLICATIONS

Blaney, Jeffrey M., et al., Chemical Reviews (A.C.S.), vol. 84 No. 4 (1984), pp. 333–407.
Manteuffel–Cymbrowska, Malgorzata, et al., J. Insect. Physiol. vol. 16, (1970), pp. 1419–1428.
Coats et al, QSAR, Des. Bioact. CMPD., 71–85 (1984).
R.L. Blakeley, "The Biochemistry of Folic Acid and Related Pteridines", pp. 464–469, (1969) John Wiley & Sons, Inc. N.Y.
Pteridines. XXXIX. Synthesis of 2,4–Diamino–7–alkenylpteridines and Their Oxides, [E.C. Taylor and T. Kobayashi; JOC.; 41 (8), 1299 (1975)].
Pteridines. XXIX. An Unequivocal Route to 2,4–Diamino–6–substituted Pteridines. [E.C. Taylor, et al., JACS.; 95, 6414 (1973)].
2,4,7–Triamino–6–ortho–substituted Arylpteridines. A new Series of Potent Antimalarial Agents [T.S. Osdene,P.B. Russell; J.Med.Chem.; 10, 431 (1967)].
Pteridines. 51. A new and Unequivocal Route to C–6 Carbon–substituted Pterins and pteridines [E.C. Taylor and P.S. Ray; JOC, 53, 3997 (1987)].
CA 51 : 13870c (1957).
CA 51 : 13874c,d (1957).
CA 51 : 13944c (1957).
CA 58 : 12546g (1963).
CA 60 : 2983c (1963).
CA 60 : 15892h (1964).
CA 62 : 6496 f, g (1964).
CA 69 : 52104f (1968), Weinstack et al.
CA 69 : 6733g (1968).
CA 79 : 78742u (1973).
CA 79 : 137092g (1973).
CA 80 : 37071b (1973).
CA 98 : 179319j (1982).
CA 103 : 17456c (1984).
CA 103 : 87712a (1985).
CA 104 : 149407m (1985).
CA 108 : 37481g (1988).

(List continued on next page.)

Primary Examiner—Richard L. Raymond
Attorney, Agent, or Firm—Stanford M. Back; Robert M. Kennedy

[57] ABSTRACT

This invention relates to pteridine and 8-deazapteridine compounds and compositions containing the same which are useful for controlling insects in agricultural crops. These pteridines may be represented by the following structure:

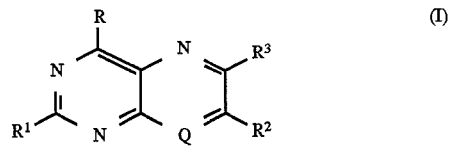

wherein
R and $R^1$ are independently selected from amino, lower alkylamino, di(lower alkyl)amino (e.g., —N(CH$_3$)$_2$), or di(lower alkyl)aminomethyleneamino (e.g., —N=CHN(CH$_3$)$_2$);

$R^2$ is hydrogen, amino, lower alkyl (e.g., —CH$_3$, —CH(CH$_3$)$_2$), di(lower alkyl)aminomethyleneamino, hydroxy, lower alkoxy, phenyl or substituted phenyl, haloalkylphenylalkyl (e.g., 3-trifluoromethylphenylmethyl);

Q is N or CH;

$R^3$ is -(n)$_m$-$R^4$, where m is 0 or 1; wherein, when m is 1, n is a bridging atom or moiety selected from oxygen, sulfur, sulfinyl, sulfonyl, lower alkylene (e.g., —CH$_2$—, or —CH$_2$CH$_2$—), lower alkenylene (e.g., —CH=CH—), lower alkynylene (e.g., —C≡C—), lower haloalkenylene (e.g., —C(Cl)=CH—), carbonyl, aminomethyl (e.g., —CH$_2$NH—), or (substituted amino)methyl (e.g., —CH$_2$N(CH$_3$)—); and $R^4$ is hydrogen, lower alkyl (e.g., —CH$_3$, or —CH(CH$_3$)$_2$), thien-2-yl, pyridin-3-yl, or

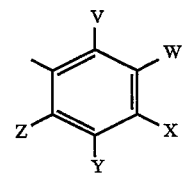

wherein
(i) V, W, X, Y, and Z are as defined herein.

19 Claims, No Drawings

OTHER PUBLICATIONS

CA 117 : 171385t (1992).

CA 120 : 4377x (1993), Clio et al.

Bhallo et al., Chemical Abstracts, vol. 68, abstract 104123n. 1968.

Landa et al., Chemical Abstracts, vol. 77 abstract 97723p. 1972.

Saska et al., Chemical Abstracts, vol. 77 abstract 135798b. 1972.

Haynes et al., Chemical Abstracts, vol. 79 abstract 88274g. 1973.

INSECTICIDAL PTERIDINES AND 8-DEAZAPTERIDINES

This application is a continuation of application Ser. No. 08/067,897, filed May 27, 1993, now U.S. Pat. No. 5,521,190.

BACKGROUND OF THE INVENTION

This invention relates to pteridine and 8-deazapteridine compounds and compositions containing the same which are useful for controlling insects in agricultural crops. More particularly, this invention relates to certain 2,4-diaminopteridine and 2,4-diamino-8-deazapteridine compounds and compositions, and their use as insecticides against a variety of insects, including larvae, such as the tobacco budworm. Certain of the pteridine compounds employed herein, and their preparation, have been described in the literature for use in a variety of fields, but not as insecticides.

SUMMARY OF THE INVENTION

In accordance with the present invention it has been found that certain defined substituted-pteridines, more particularly 2,4-diaminopteridines and 2,4-diamino-8-deazapteridines, and agriculturally acceptable salts thereof, when present in insecticidally effective amounts, and with a suitable agricultural carrier, are useful as active ingredients in the insecticidal compositions and methods of this invention. These pteridines may be represented by the following structure:

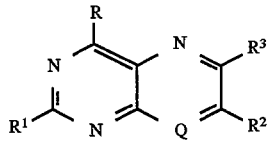
(I)

wherein

R and $R^1$ are independently selected from amino, lower alkylamino, di(lower alkyl)amino (e.g., —$N(CH_3)_2$), or di(lower alkyl)aminomethyleneamino (e.g., —N=$CHN(CH_3)_2$);

$R^2$ is hydrogen, amino, lower alkyl (e.g., —$CH_3$, —CH$(CH_3)_2$), di(lower alkyl)aminomethyleneamino, hydroxy, lower alkoxy, phenyl or substituted phenyl, haloalkylphenylalkyl (e.g., 3-trifluoromethylphenylmethyl);

Q is N or CH;

$R^3$ is -(n)$_m$-$R^4$, where m is 0 or 1; wherein
when m is 1, n is a bridging atom or moiety selected from oxygen, sulfur, sulfinyl, sulfonyl, lower alkylene (e.g., —$CH_2$— or —$CH_2CH_2$—), lower alkenylene (e.g., —CH=CH—), lower alkynylene (e.g., —C≡C—), lower haloalkenylene (e.g., —C(Cl)=CH—), carbonyl, aminomethyl (e.g., —$CH_2NH$—), or (substituted amino)methyl (e.g., —$CH_2N(CH_3)$—); and $R^4$ is hydrogen, lower alkyl (e.g., —$CH_3$ or —$CH(CH_3)_2$), thien-2-yl, pyridin-3-yl, or

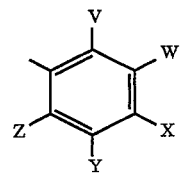

wherein

V, W, X, Y, and Z are independently selected from the group consisting of hydrogen, halogen (e.g., Cl, F), lower alkyl (e.g., —$CH_3$, or —$C(CH_3)_3$), lower alkoxy (e.g., —$OCH_3$), lower haloalkyl (e.g., —$CF_3$), cyano, lower alkoxycarbonyl (e.g., —$CO_2CH_3$), aminocarbonyl, phenyl optionally substituted with chloro, fluoro, or trifluoromethyl; or phenoxy optionally substituted with chloro, fluoro, or trifluoromethyl; wherein optionally V and W taken together form a fused ring and are —$OC(CH_3)_2CH_2$—, —$CH_2C(CH_3)_2O$—, —$OC(CH_3)_2C(=O)$—, —$C(=O)C(CH_3)_2O$—, —$OCF_2CF_2$—, or —$CF_2CF_2O$—, to provide, respectively, the corresponding 2,3-dihydro-2,2-dimethylbenzofuran-7-yl, 2,3-dihydro-2,2-dimethylbenzofuran-4-yl, 2,3-dihydro-2,2-dimethyl-3-benzofuranon-7-yl, 2,3-dihydro-2,2-dimethyl-3-benzofuranon-4-yl, 2,2,3,3-tetrafluorobenzofuran-7-yl, and 2,2,3,3-tetrafluorobenzofuran-4-yl moieties; or, optionally, V and W or W and X taken together are —CH=CHCH=CH—, forming the corresponding naphth-1-yl and naphth-2-yl rings.

Of these compounds, among the more preferred ones in addition to certain other novel ones identified below for use in the compositions and methods of this invention, are those wherein the pteridines and 8-deazapteridines are; of the structure (I) above, and wherein
a)
R and $R^1$ are amino;
$R^2$ is hydrogen or lower alkyl, e.g. (—$CH_3$);
Q is N or CH;
$R^3$ is -(n)$_m$-$R^4$, where m is 0; and
$R^4$ is

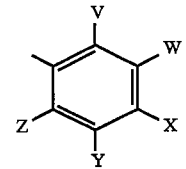

wherein

Z and X are independently selected from hydrogen and fluoro; and V, W, and Y are independently selected from hydrogen, halogen, lower haloalkyl, carboxy, lower alkoxycarbonyl, phenyl, and phenyl substituted with halogen or lower haloalkyl, phenoxy and phenoxy substituted with halogen or lower haloalkyl, V and W taken together form a fused ring and are —$OC(CH_3)_2CH_2$—,—$CH_2C(CH_3)_2O$—, —$OC(CH_3)_2C(=O)$—, —$C(=O)C(CH_3)_2O$—, with the proviso that at least one of V, W, or Y must be a substituent other than hydrogen; and b)
R and $R^l$ are amino;
$R^2$ is hydrogen or lower alkyl (—$CH_3$);

Q is N or CH;

R³ is -(n)ₘ-R⁴, where m is 1, n is carbonyl or lower haloalkenylene (e.g. —C(Cl)=CH—), and R⁴ is

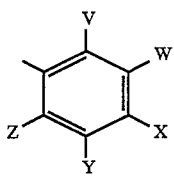

wherein

V, W, X, and Y are independently selected from hydrogen, halogen, lower haloalkyl, phenyl, phenyl substituted with halogen or lower haloalkyl, phenoxy, or phenoxy substituted with halogen or lower haloalkyl, and Z is hydrogen or halogen.

In a further embodiment, this invention is also directed to certain novel substituted pteridines and 8-deazapteridines per se falling within the scope of structure (I) above. These compounds, as illustrated, for example, by Compounds 5, 7–24, 32–42, 65–70, and 76–234 of Table I below, include the following novel pteridines and 8-deazapteridines, which in the same manner as the above compounds, may be prepared by methods that are provided in the detailed synthesis description below and in the accompanying Examples 1,2, 4–12:

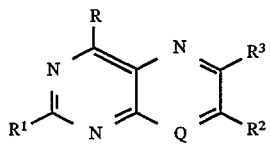

(I)

wherein

R and R¹ are amino;

R² is hydrogen or lower alkyl (—CH₃);

Q is N or CH;

R³ is -(n)ₘ-R⁴ where m is 0 or 1, and when m is 1, n is carbonyl or lower haloalkenylene (e.g, —C(Cl)=CH—); and R⁴ is

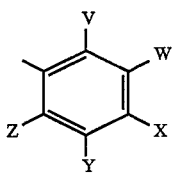

wherein

V, W, X, Y, and Z are independently selected from the group consisting of hydrogen, halogen (e.g., Cl, F), lower alkyl (e.g., —CH₃ or —C(CH₃)₃), lower alkoxy (e.g., —OCH₃), lower haloalkyl (e.g., —CF₃), cyano, lower alkoxycarbonyl (e.g., —CO₂CH₃), aminocarbonyl, phenyl optionally substituted with chloro, fluoro, or trifluoromethyl; or phenoxy optionally substituted with chloro, fluoro, or trifluoromethyl; wherein optionally V and W taken together form a fused ring and are —OC(CH₃)₂CH₂—, —CH₂C(CH₃)₂O—, —OC(CH₃)₂C(=O)—, —C(=O)C(CH₃)₂O—, —OCF₂CF₂—, or —CF₂CF₂O—, to provide, respectively, the corresponding 2,3-dihydro-2,2-dimethylbenzofuran-7-yl, 2,3-dihydro-2,2-dimethylbenzofuran-4-yl, 2,3-dihydro-2,2-dimethyl-3-benzofuranon-7-yl, 2,3-dihydro-2,2-dimethyl-3-benzofuranon-4-yl, 2,2,3,3-tetrafluorobenzofuran-7-yl, and 2,2,3,3-tetrafluoro-benzofuran-4-yl moieties; or, optionally, V and W or W and X taken together are —CH=CHCH=CH—, forming the corresponding naphth-1-yl and naphth-2-yl rings.

Of these novel compounds, particularly preferred ones include those wherein the pteridines and 8-deazapteridines are of the general structure (I) above, and wherein, when m is 0, (i) V, X and Z are hydrogen, and W and Y are halogen or trifluoromethyl (Compounds 9, 13, 34, 37, 79, 83, 98, and 101);

(ii) W, X, Y, and Z are hydrogen, and V is 4-chlorophenyl (Compounds 21 and 91);

(iii) V, X, Y, and Z are hydrogen, and W is 4-fluorophenyl (Compounds 41 and 105); and (iv) X and Z are hydrogen, Y is hydrogen or chloro, and V and W taken together form a fused ring with —OC(CH₃)₂CH₂—, —CH₂C(CH₃)₂O—, —OC(CH₃)₂C(=O)—, and —C(=O)C(CH₃)₂O— (Compounds 17, 18, 87, 88, 231, and 233).

Also preferred amongst the novel compounds of this invention are those wherein, when m is 1, and n is carbonyl, (i) V, X, and Z are hydrogen, and W and Y are trifluoromethyl (Compounds 142, 166, 190, and 214);

(ii) V, X, Y, and Z are hydrogen, and W is 4-trifluoromethylphenyl (Compounds 155, 179, 203, and 227), and;

(iii) V, W, Y, and Z are hydrogen, and X is 4-fluorophenyl (Compounds 156, 180, 204 and 228).

Other preferred novel compounds within the scope of structure (I), above, include those wherein, when m is 1, and n is lower haloalkenylene (e.g., —C(Cl)=CH—), (i) V, W, Y, and Z are hydrogen, and X is chloro or trifluoromethyl (Compounds 108, 112, 115, 119, 122, 126, 129, and 133).

All of the above compounds are preferred because of their high insecticidal activity. They may be used in controlling insects by applying to the locus where control is desired an insecticidal amount of these compounds admixed in a suitable agricultural carrier. When thus applied to insect-infected crops such as cotton, vegetables, fruits or other crops, these compounds are highly effective against an array of insects, particularly those shown in the tables below.

For the purposes of this invention, as regards the above substituent groups, the following definitions apply:

The term alkyl includes straight or branch chained alkyl of 1 to 14 carbon atoms, preferably lower straight or branched alkyl of 1 to 6 carbon atoms; while halogen includes chlorine, bromine, fluorine and iodine atoms. The terms haloalkyl and haloalkoxy include straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl and 2,2,2-trifluoroethoxy, respectively. The terms lower alkoxy and lower dialkylamino include those moieties having 1 to 6 carbon atoms, e.g., ethoxy and N,N-dimethylamino, respectively.

The terms aryl and substituted aryl include phenyl, naphthyl, 2,3-dihydro-2,2-dimethylbenzofuran-7-yl, 2,3-dihydro-2,2-dimethylbenzofuran-4yl, 2,3-dihydro-2,2- dimethyl-3-benzofuranon-7-yl, 2,3-dihydro-2,2-dimethyl3-benzofuranon-4-yl, 2,2,3,3-tetrafluorobenzofuran-7-yl, and 2,2,3,3-tetrafluorobenzofuran-4-yl; preferably phenyl or substituted phenyl, while the terms aryl and substituted aryl include benzoyl and naphthoyl, preferably benzoyl or substituted benzoyl. The terms substituted aryl and aroyl include those groups substituted with one or more alkyl, halo, alkoxy, or haloalkyl groups, or the like.

In addition, the term arylalkyl includes 2-(naphth-2-yl)ethyl; arylalkenyl includes 2-(naphth-2-yl)ethenyl; arylthio includes 3,4-dichlorophenylthio and naphth-2-ylthio; arylsulfinyl includes 3,4-dichloroethylsulfinyl and naphth-2-ylsulfinyl; while arylsulfonyl includes 3,4-dichlorophenylsulfonyl and naphth-2-ylsulfonyl.

DETAILED DESCRIPTION OF THE INVENTION

Synthesis of the Compounds

The compounds employed as insecticides in accordance with this invention are generally known to those skilled in the art, including commercial preparations thereof, or may readily be prepared from these compounds by known methods. These and other methods are described in further detail in the description and examples below.

Thus, for example, using a method disclosed by T. S. Osdene and P. B. Russell [J. Med. Chem., 10, 431, (1967)], those compounds wherein Q is nitrogen, R and $R^1$ are amino, and $R^2$ is methyl or amino, may be prepared by the reaction of either an appropriately substituted acetone, for example, (3,4-dichlorophenyl)acetone (where $R^2$ is —$CH_3$), or an appropriately substituted acetonitrile, for example, 2-chlorophenylacetonitrile (where $R^2$ is —$NH_2$) with 2,4,6-triamino-5-nitrosopyrimidine under basic conditions in dimethylformamide, 2-methoxyethanol, or 1,2-diethoxymethane, yielding the corresponding 2,4-diamino-6-substituted-7-methylpteridines or the 2,4,7-triamino-6-substituted-pteridines, for example, 2,4-diamino-6-(3,4-dichlorophenyl)-7-methylpteridine or 2,4,7-triamino-6-(2-chlorophenyl)pteridine. Examples 1 and 2 describe in detail the manner in which these compounds are prepared.

The 2,4,7-triamino-6-substituted-pteridines prepared as described above may readily be derivatized. For example, 2,4,7-triamino-6-(2-chlorophenyl)pteridine when heated with N,N-dimethylformamide dimethylacetal, yields the corresponding 2,4,7-tri(dimethylaminomethyleneamino)-6-(2-chlorophenyl)pteridine. Example 3 describes in detail the manner in which this compound is prepared.

Other compounds wherein Q is nitrogen or CH, R and $R^1$ are amino, and $R^2$ is hydrogen or methyl, may be prepared by the reaction of, for example, 2-amino-3-cyano-5-bromopyrazine, 2-amino-3-cyano-5-bromo-6-methylpyrazine, or 3-amino-2-cyano-6-chloropyridine with an optionally substituted phenylboronic acid, or a more complex boronic acid such as 2,3-dihydro-3-hydroxy-2,2-dimethylbenzofuran-7-ylboronic acid, under basic conditions in the presence of tetrakis(triphenylphosphine)palladium(0) in toluene, which produce, respectively, the corresponding 2-amino-3-cyano-5-(optionally substituted phenyl)pyrazines, 2-amino-3-cyano-5-(optionally substituted phenyl)-6-methylpyrazines, 3-amino-2-cyano-6-(optionally substituted phenyl)pyridines, 2-amino-3-cyano-5-(2,3-dihydro-3-hydroxy-2,2-dimethylbenzofuran-7-yl)pyrazines, 2-amino-3-cyano-5-(2,3-dihydro-3-hydroxy-2,2-dimethylbenzofuran-7-yl)-6-methylpyrazines, or 3-amino-2-cyano-6-(2,3-dihydro-3-hydroxy-2,2-dimethylbenzofuran-7-yl)pyridines. The thus-prepared pyrazines and pyridines may then be cyclized with guanidine carbonate in N,N-dimethylacetamide, guanidine hydrochloride in sodium methoxide/methanol, or chloroformamidine hydrochloride in diglyme, affording the desired 6-(optionally substituted phenyl)pteridines and 8-deazapteridines, or the more complex 6-substituted pteridines and 8-deazapteridines, for example, the 6-(2,3-dihydro-3-hydroxy-2,2-dimethylbenzofuran-7-yl)pyrazines. Examples 4, 5, 7, and 12 describe in detail how these compounds are prepared.

Certain of the 6-substituted pteridines and 8-deazapteridines, whose preparation is described directly above, may be reacted further to give other 6-substituted pteridines and 8-deazapteridines. For example, 2,4-diamino-6-(2,3-dihydro-3-hydroxy-2,2-dimethylbenzo-furan-7-yl)pteridine is oxidized to the corresponding 2,4-diamino-6-(2,3-dihydro-2,2-dimethyl-3-benzofuranon-7-yl)pteridine using a method disclosed by D. Swern [Tetrahedron, 34, 1651–1660 (1978)]. Step G of Example 12 describes in detail how this compound is prepared.

Compounds wherein Q is nitrogen or CH, R and $R^1$ are amino, and $R^2$ is hydrogen or methyl may be prepared using the method of Beletskaya et al. [Dokl. Akad. Nauk. SSSR, 320(3), 619–622 (1991)], i.e., by the carbonylation of 2-amino-3-cyano-5-bromopyrazine or 2-amino-3-cyano-5-bromo-6-methylpyrazine under about one atmosphere of pressure with carbon monoxide and tetramethylammonium tetra(optionally substituted phenyl)borate in the presence of a catalytic amount of palladium acetate, which affords the corresponding 2-amino-3-cyano-5-(optionally substituted phenylcarbonyl)pyrazines or the 2-amino-3-cyano-5-(optionally substituted phenylcarbonyl)-6-methylpyrazines. The so-prepared pyrazines may then be cyclized with chloroformamidine hydrochloride in diglyme, affording the desired 6-(optionally substituted phenylcarbonyl)pteridines. Example 8 describes in detail how these compounds are prepared.

Applying the method of Beletskaya et al. as described above, and using 3-amino-2-cyano-6-iodopyridine, the resulting 2-amino-3-cyano-6-(optionally substituted phenylcarbonyl)pyridines may then be cyclized with chloroformamidine hydrochloride in diglyme, affording the desired 6-(optionally substituted phenylcarbonyl)-8-deazapteridines. Example 10 describes in detail how these compounds are prepared.

Yet other compounds wherein Q is nitrogen or CH, R and $R^1$ are amino, and $R^2$ is hydrogen or methyl may be prepared by the reaction of, for example, 2-amino-3-cyano-5-bromopyrazine, 2-amino-3-cyano-5-bromo-6-methylpyrazine, or 3-amino-2-cyano-6-iodopyridine with (trimethylsilyl)acetylene under basic conditions in the presence of catalytic amounts of bis(triphenylphosphine)palladium(II) chloride and copper iodide, to provide the corresponding 5-(trimethylsilylethynyl)pyrazines and 6-(trimethylsilylethynyl)pyridines. Treatment of the trimethylsilylethynyl derivatives with potassium carbonate then affords the corresponding the 5-(ethynyl)pyrazines and 6-(ethynyl)pyridines, which may in turn be reacted with an optionally substituted phenyl halide under basic conditions in the presence of catalytic amounts of bis(triphenylphosphine)palladium(II) chloride and copper iodide, affording the corresponding 5-[(optionally substituted phenyl)ethynyl]pyrazines and 6-[(optionally substituted phenyl)ethynyl]pyridines. Cyclization of the thus-prepared 5-[(optionally substituted phenyl)ethynyl]pyrazines and 6-[(optionally substituted phenyl)ethynyl]pyridines with chloroformamidine hydrochloride in diglyme, as previously described, provides the desired 6-[1-chloro-2-(optionally substituted phenyl)ethenyl]pteridines and 8-deazapteridines. Examples 9 and 11 describe in detail how these compounds are prepared.

The intermediate pyrazines and pyridines used in this reaction may be prepared according to methods found in references from the open literature. The intermediate 2-amino-3-cyano-5-bromopyrazine may be prepared according to the method of Taylor and Ray [JOC, 52, 3997, (1987)], while the intermediate 2-amino-3-cyano-5-bromo-6-methylpyrazine may be prepared by the method of Taylor and Kobayashi [JOC, 41, 1299 (1976)]. The intermediate 3-amino-2-cyano-6-chloropyridine, prepared by the method of Colbry, Elslager, and Werbel [J. Het. Chem., 21, 1521 (1984)], may be converted to 3-amino-2-cyano-6-iodopyridine by the method of Setliffe and Price [J. Chem. Eng. Data, 18(4), 449 (1973)].

The optionally substituted phenylboronic acid intermediates are either commercially available or may be prepared by the method of Thompson and Gaudino [JOC, 49, 5237 (1984)].

In an alternative route, intermediates to those compounds wherein Q is nitrogen, R and $R^1$ are amino, and $R^2$ is hydrogen or methyl may be prepared by the method of Taylor, Perlman, et al. [JACS, 95, 6413 (1973)]. Thus, the reaction of a phenylglyoxaldoxime, for example, the oxime of 3,5-dichlorophenylglyoxaldoxime (where $R^2$ is hydrogen), with aminomalononitrile p-toluenesulfonate in 2-propanol affords the corresponding 2-amino-3-cyano-5-(optionally substituted phenyl)pyrazine 1-oxides, for example, 2-amino-3-cyano-5-(3,5-dichlorophenyl)pyrazine 1-oxide. The pyrazine 1-oxides may in turn be reduced with phosphorus trichloride in tetrahydrofuran, yielding the corresponding 2-amino-3-cyano-5-(optionally substituted phenyl)pyrazines. The pyrazines may then be cyclized with guanidine carbonate in N,N-dimethylacetamide, as previously described, yielding the desired 2,4-diamino-6-(optionally substituted phenyl)pteridines, for example, 2,4-diamino-6-(3,5-dichlorophenyl)pteridine. Example 6 describes in detail how these compounds are prepared.

EXAMPLES

The following examples are by way of illustration only, and are not intended to limit the scope of the invention claimed herein.

The products of these examples are summarized in Table 1 below.

EXAMPLE 1

SYNTHESIS OF 2,4-DIAMINO-6-(3,4-DICHLOROPHENYL)-7-METHYLPTERIDINE (COMPOUND 34)

Step A Synthesis of N-methoxy-N-methyl-3,4-dichlorophenyl acetamide as an intermediate A solution of 20.3 grams (0.098 mole) of 3,4-dichlorophenylacetic acid in 200 mL of methylene chloride was stirred, and 10.7 mL (0.124 mole) of oxalyl chloride was added in one portion, followed by 6 drops of N,N-dimethylformamide. Upon completion of addition, the reaction mixture was stirred at ambient temperature for about 18 hours. After this time, 12.0 grams (0.123 mole) of N,O-dimethylhydroxylamine hydrochloride was added in one portion. The reaction mixture was then cooled to 0° C., and 35.9 mL (0.450 mole) of pyridine was added dropwise during a 45 minute period. Upon completion of addition, the reaction mixture was allowed to warm to ambient temperature, where it was stirred for about 18 hours. The reaction mixture was then diluted with 200 mL of water, and the organic layer was separated. The organic layer was washed with 200 mL of an aqueous solution saturated with sodium chloride. The organic layer was dried with sodium sulfate and filtered. The filtrate was concentrated under reduced pressure to a residue. The residue was subjected to column chromatography on silica gel. Elution was accomplished using 5% ethyl acetate in methylene chloride, then gradually increasing to 15% ethyl acetate in methylene chloride. The product-containing fractions were combined and concentrated under reduced pressure, yielding 19.4 grams of N-methoxy-N-methyl-3,4-dichlorophenylacetamide. The NMR spectrum was consistent with the proposed structure.

Step B Synthesis of (3,4-dichlorophenyl)acetone as an intermediate

Tetrahydrofuran, 75 mL, was cooled to 0° C., and 10.3 mL of methylmagnesium iodide (3.0M in diethyl ether) was added dropwise during a 30 minute period. The reaction mixture was maintained at <2° C. during the addition. Upon completion of addition, 7.0 grams (0.028 mole) of N-methoxy-N-methyl-3,4-dichlorophenylacetamide was added dropwise during a 45 minute period. The reaction mixture temperature was maintained between −2° C. and +2° C. throughout the addition. Upon completion of addition, the reaction mixture was stirred at about 0° C. for 1.5 hours. After this time, 50 mL of aqueous 2N hydrochloric acid was added dropwise to the reaction mixture. The reaction mixture temperature was maintained at <4° C. throughout the addition. The reaction mixture was then taken up in 100 mL of water and extracted with two 150 mL portions of diethyl ether. The combined extracts were washed with 100 mL of an aqueous solution saturated with sodium chloride. The extracts were then dried with magnesium sulfate and filtered. The filtrate was concentrated under reduced pressure to a residue, which weighed 6.6 grams. The 6.6 grams isolated here was combined with 3.2 grams of the same material prepared in an analogous manner. The combination was subjected to column chromatography on silica gel. Elution was accomplished using 50% methylene chloride in petroleum ether, then gradually increasing to 75% methylene chloride in petroleum ether. The product-containing fractions were combined and concentrated under reduced pressure, yielding 3.4 grams of (3,4-dichlorophenyl)acetone. The NMR spectrum was consistent with the proposed structure.

Step C Synthesis of 2,4-diamino-6-(3,4-dichlorophenyl)-7-methylpteridine (Compound 34)

A stirred solution of 1.0 gram (0.007 mole) of 2,4,6-triamino-5nitrosopyrimidine and 2.7 grams (0.020 mole) of potassium carbonate in 30 mL of N,N-dimethylformamide was heated to 95°–100° C., and 2.0 grams (0.010 mole) of (3,4-dichlorophenyl)acetone was added in one portion. Upon completion of addition, the reaction mixture was allowed to cool to ambient temperature, where it was allowed to stir for about 18 hours. After this time the reaction mixture was concentrated under reduced pressure. The residue was triturated with 250 mL of water, and the remaining solid was collected by filtration. The solid was further triturated with 50 mL of 20% methanol in methylene chloride. The remaining solid was collected by filtration, yielding 0.5 gram of 2,4-diamino-6-(3,4-dichlorophenyl)-7-methylpteridine. The NMR spectrum is consistent with the proposed structure.

EXAMPLE 2

SYNTHESIS OF 2,4,7-TRIAMINO-6-(2-CHLOROPHENYL)PTERIDINE

(COMPOUND 48)

A stirred solution of 1.5 grams (0.010 mole) of 2,4,6-triamino-5-nitrosopyrimidine in 80 mL of N,N-dimethylformamide was heated to reflux, and 2.0 grams (0.013 mole) of 2-chlorophenylacetonitrile was added in one portion. Upon completion of addition, the reaction mixture was cooled, and 0.7 gram (0.013 mole) of sodium methoxide was added in one portion. The reaction mixture was again heated at reflux for 15 minutes. The reaction mixture was cooled in an ice-bath and then was filtered to collect a solid. The solid was slurried in diethyl ether and then was again collected by filtration, yielding, when dried, 2.5 grams of 2,4,7-triamino-6-(2-chlorophenyl)pteridine. The NMR spectrum was consistent with the proposed structure.

NOTE: This compound was prepared in a manner disclosed by Osdene and Russell—[J. Med. Chem., 10, 431, (1967)]

EXAMPLE 3

SYNTHESIS OF 2,4,7-TRI (DIMETHYLAMINOMETHYLENEAMINO)-6-(2-CHLOROPHENYL)PTERIDINE

(COMPOUND 66)

Under a nitrogen atmosphere, a stirred solution of 0.5 gram (0.002 mole) of 2,4,7-triamino-6-(2-chlorophenyl) pteridine (prepared in Example 2) in 50 mL of N,N-dimethylformamide dimethylacetal was heated at reflux for about 5 hours. After this time the reaction mixture was cooled in an ice-bath, and a solid was collected by filtration. The solid was washed with diethyl ether, yielding, when dried, 0.5 gram of 2,4,7-tri-(dimethylaminomethyleneamino)-6-(2-chlorophenyl) pteridine. The NMR spectrum was consistent with the proposed structure.

EXAMPLE 4

SYNTHESIS OF 2,4-DIAMINO-6-[3,5-DI (TRIFLUOROMETHYL)PHENYL]PTERIDINE

(COMPOUND 13)

Step A Synthesis of 2-amino-3-cyano-5-[3,5-di (trifluoromethyl)-phenyl]pyrazine as an intermediate A stirred solution of 1.6 grams (0.008 mole) of 2-amino-3-cyano-5-bromopyrazine [prepared by the method of Taylor and Ray—JOC, 52, 3997 (1987)], 3.2 grams (0.012 mole) of 3,5-di(trifluoromethyl)phenylboronic acid [commercially available or prepared by the method of Thompson and Gaudino—JOC, 49, 5237 (1984)], 4.3 grams (0.031 mole) of potassium carbonate and 0.3 gram of tetrakis(triphenylphosphine)palladium(0) in 150 mL of toluene is heated at 90° C. for about 20 hours. After this time, the reaction mixture is stirred with 100 mL of water, and the organic layer is separated. The organic layer is concentrated under reduced pressure to a residue. The residue is subjected to column chromatography on silica gel. The product-containing fractions are combined and concentrated under reduced pressure, yielding 2-amino-3-cyano-5-[3,5-di (trifluoromethyl)phenyl]pyrazine.

Step B Synthesis of 2,4-diamino-6-[3,5-di(trifluoromethyl) phenyl]pteridine (Compound 13)

Under a nitrogen atmosphere, a stirred solution of 1.0 gram (0.003 mole) of 2-amino-3-cyano-5-[3,5-di (trifluoromethyl)phenyl]pyrazine and 1.3 grams (0.007 mole) of guanidine carbonate in 10 mL of N,N-dimethylacetamide is heated at about 150° C. for 40 hours. After this time, the reaction mixture is poured into 50 mL of water. The resultant solid is collected by filtration and is then slurried in 25 mL of diethyl ether. The solid is again collected by filtration and is then recrystallized from ethanol, yielding 2,4-diamino-6-[3,5-di(trifluoromethyl) phenyl]pteridine.

EXAMPLE 5

SYNTHESIS OF 2,4-DIAMINO-6-[3,5-DI (TRIFLUOROMETHYL)PHENYL]-7-METHYLPTERIDINE

(COMPOUND 37)

Step A Synthesis of 2-amino-3-cyano-5-bromo-6-methylpyrazine as an intermediate

A stirred solution of 8.5 grams (0.063 mole) of 2-amino-3-cyano-6-methylpyrazine [prepared by the method of Taylor and Kobayashi; JOC, 41, 1299 (1976)]in 125 mL of N,N-dimethylformamide is cooled in an ice bath, and a solution of 11.2 grams (0.063 mole) of N-bromosuccinimide in 125 mL of N,N-dimethylformamide is added dropwise during a 30 minute period, while maintaining the reaction mixture temperature at about 15°–25° C. Upon completion of addition, the reaction mixture is stirred at ambient temperature for about 20 hours. After this time, the reaction mixture is poured into 1 liter of aqueous 3N sodium hydroxide. The mixture is then diluted to a volume of about 1700 mL with distilled water. A solid precipitate is collected by filtration and dried under reduced pressure, yielding 2-amino-3-cyano-5-bromo-6-methylpyrazine.

Step B Synthesis of 2-amino-3-cyano-5-[3,5-di (trifluoromethyl)phenyl]-6-methylpyrazine as an intermediate This compound is prepared in a manner analogous to that of Step A of Example 4, using 1.7 grams (0.008 mole) of 2-amino-3-cyano-5-bromo-6-methylpyrazine, 3.2 grams (0.012 mole) of 3,5-di(trifluoromethyl)phenylboronic acid, 4.3 grams (0.031 mole) of potassium carbonate and 0.3 gram of tetrakis(triphenylphosphine)palladium(0)in 150 mL of toluene, yielding 2-amino-3-cyano-5-[3,5-di(trifluoromethyl)phenyl]-6-methylpyrazine.

Step C Synthesis of 2,4-diamino-6-[3,5-di(trifluoromethyl) phenyl]-7-methylpteridine (Compound 37)

This compound is prepared in a manner analogous to that of Step B of Example 4, using 1.1 grams (0.003 mole) of 2-amino-3-cyano-5-[3,5di(trifluoromethyl)phenyl]-6-methylpyrazine and 1.3 grams (0.007 mole) of guanidine carbonate in 10 mL of N,N-dimethylacetamide, yielding 2,4-diamino-6-[3,5-di(trifluoromethyl)phenyl]-7-methylpteridine.

EXAMPLE 6

SYNTHESIS OF 2,4-DIAMINO-6-(3,5-DICHLOROPHENYL)PTERIDINE

(COMPOUND 9)

Step A Synthesis of 2-amino-3-cyano-5-(3,5-dichlorophenyl)pyrazine 1-oxide as an intermediate A suspension of 43.6 grams (0.2 mole) of 3,5-dichlorophenylglyoxaldoxime and 50.6 grams (0.2 mole) of aminomalononitrile p-toluene-sulfonate in 300 mL of 2-propanol is stirred at ambient temperature for 4 hours. The solid product is collected from the reaction mixture by filtration, and washed with a small amount of cold water. The solid is dried, yielding 2-amino-3-cyano-5-(3,5-dichlorophenyl)pyrazine 1-oxide.

Step B Synthesis of 2-amino-3-cyano-5-(3,5-dichlorophenyl)pyrazine as an intermediate A stirring solution of 5.5 grams (0.02 mole) of 2-amino-3-cyano-5-(3,5-dichlorophenyl)pyrazine 1-oxide in 200 mL of dry tetrahydrofuran is cooled to 0° C. and 30 mL of phosphorus trichloride is added dropwise during a 5 minute period. Upon completion of addition, the reaction mixture is stirred at ambient temperature for 40 minutes. After this time the reaction mixture is concentrated under reduced pressure to about 50 mL. The 50 mL of concentrate is poured into 1000 mL of ice-water. The resultant solid is collected by filtration and dried, yielding 2-amino-3-cyano-5-(3,5-dichlorophenyl)pyrazine.

Step C Synthesis of 2,4-diamino-6-(3,5-dichlorophenyl) pteridine (Compound 9)

This compound is prepared in a manner analogous to that of Step B of Example 4, using 0.8 gram (0.003 mole) of 2-amino-3-cyano-5-(3,5-dichlorophenyl)pyrazine and 1.3 grams (0.007 mole) of guanidine carbonate in 10 mL of N,N-dimethylacetamide, yielding 2,4-diamino-6-(3,5-dichlorophenyl)pteridine.

NOTE: The method of Taylor, Perlman, et al. [(JACS, 95, 6413 (1973)] is used for the synthesis of intermediates that are shown in Steps A and B of Example 6.

EXAMPLE 7

SYNTHESIS OF 2,4-DIAMINO-6-[3,5-DI (TRIFLUOROMETHYL)PHENYL]-8-DEAZAPTERIDINE (COMPOUND 83)

Step A Synthesis of 3-amino-2-cyano-6-[3,5-di (trifluoromethyl)phenyl]pyridine as an intermediate This compound is prepared in a manner analogous to that of Step A of Example 4, using 1.2 grams (0.008 mole) of 3-amino-6-chloro-2-cyanopyridine [prepared by the method of Colbry, Elslager, and Werbel; J. Het. Chem.; 21, 1521 (1984)], 3.2 grams (0.012 mole) of 3,5-di(trifluoromethyl) phenylboronic acid, 4.3 grams (0.031 mole) of potassium carbonate and 0.3 gram of tetrakis(triphenylphosphine) palladium(0)in 150 mL of toluene, yielding 3-amino-2-cyano-6-[3,5-di(trifluoromethyl)phenyl]pyridine.

Step B Synthesis of chloroformamidine hydrochloride as an intermediate

Diethyl ether, 600 mL, was cooled in an ice-bath and saturated with about 50 grams of hydrogen chloride gas. With vigorous stirring, a solution of 26.4 grams (0.628 mole) of cyanamide in 500 mL of diethyl ether was added during a 15 minute period. Upon completion of addition, the ice-bath was removed and the reaction mixture was allowed to stir for about 15 minutes. A white solid precipitate was collected by filtration and washed with diethyl ether. The solid was dried under reduced pressure, yielding 50.3 grams of chloroformamidine hydrochloride.

Step C Synthesis of 2,4-diamino-6-[3,5-di(trifluoromethyl) phenyl]-8deazapteridine (Compound 83)

A stirred mixture of 1.0 gram (0.003 mole) of 3-amino-2-cyano-6-[3,5di(trifluoromethyl)phenyl]pyridine and 0.3 gram (0.003 mole) of chloroformamidine hydrochloride in 11 mL of diglyme is gradually warmed to 165° C. during a 1.5 hour period. The heterogeneous mixture is maintained at 165° C. for about 4.5 hours. After this time, the reaction mixture is cooled and diluted with 200 mL of diethyl ether. The resultant precipitate, which is the hydrochloride salt of the sought-after product, is collected by filtration. The solid is converted to the free base by treating a suspension of the hydrochloride salt in hot water with 30 mL of concentrated ammonium hydroxide, then cooling the suspension in an ice bath during a 1 hour period. The resultant solid is collected by filtration, yielding 2,4-diamino-6-[3,5-di (trifluoromethyl)phenyl]-8-deazapteridine.

EXAMPLE 8

SYNTHESIS OF 2,4-DIAMINO-7-METHYL-6-PHENYLCARBONYLPTERIDINE (COMPOUND 159)

Step A Synthesis of 2-amino-3-cyano-6-methyl-5-phenylcarbonylpyrazine as an intermediate A mixture of 2.1 grams (0.010 mole) of 2-amino-3-cyano-5-bromo-6-methylpyrazine (prepared in Step A of Example 5), 4.9 grams (0.01 3 mole) of tetramethylammonium tetraphenylborate, and 0.1 gram (0.0005 mole) of palladium (II) acetate in 50 mL of N,N-dimethylformamide is placed in a high pressure reaction vessel. The stirring reaction mixture is then placed under 1 atmosphere of carbon monoxide gas, where it is maintained at about 60° C. for a 30 hour period. After this time, the cooled reaction mixture is removed from the reaction vessel and is filtered to remove catalyst and salts. The filtrate is concentrated under reduced pressure to a residue. The residue is partitioned between methylene chloride and water. The methylene chloride-product solution is then subjected to column chromatography on silica gel. Elution is accomplished with methylene chloride. The product-containing fractions are combined and concentrated under reduced pressure, yielding 2-amino-3-cyano-6-methyl-5-phenylcarbonylpyrazine.

Step B Synthesis of 2,4-diamino-7-methyl-6-phenylcarbonylpteridine (Compound 159)

This compound is prepared in a manner analogous to that of Step C of Example 7, using 2.1 grams (0.009 mole) of 2-amino-3-cyano-6-methyl-5-phenylcarbonylpyrazine and 0.9 gram (0.009 mole) chloroformamidine hydrochloride in 20 mL of diglyme, yielding 2,4-diamino-7-methyl-6-phenyl-carbonylpteridine.

EXAMPLE 9

SYNTHESIS OF 2,4-DIAMINO-6-[1—CHLORO-2-(4-TRIFLUOROMETHYLPHENYL)ETHENYL] PTERIDINE (COMPOUND 112)

Step A Synthesis of 2-amino-3-cyano-5-(trimethylsilylethynyl)pyrazine as an intermediate A solution of 3.0 grams (0.015 mole) of 2-amino-3-cyano-5-bromopyrazine and 2.1 grams (0.021 mole) of trimethyl-silylacetylene in 50 mL of acetonitrile is stirred, and 10.6 mL of triethylamine, 0.13 gram of copper iodide, and 0.29 gram of bis(triphenylphosphine)palladium(II) chloride are added in order. Upon completion of addition, the reaction mixture is stirred at ambient temperature for about 20 hours. The reaction mixture is warmed to 70° C., where it is stirred for about 7.5 hours. After this time, the reaction mixture is concentrated under reduced pressure to a residue. The residue is dissolved in ethyl acetate, and the solution is washed with 50 mL of aqueous, dilute hydrochloric acid. The organic layer is dried with magnesium sulfate and filtered. The filtrate is concentrated under reduced pressure to a residue. The residue is subjected to column chromatography on silica gel. Elution is accomplished using tetrahydrofuran/methylene chloride combinations. The product-containing fractions are combined and concentrated under reduced pressure, yielding 2-amino-3-cyano-5-(trimethylsilylethynyl)pyrazine.

Step B Synthesis of 2-amino-3-cyano-5-ethynylpyrazine as an intermediate

A mixture of 1.3 grams (0.006 mole) of 2-amino-3-cyano-5-(trimethylsilylethynyl)pyrazine and 0.9 gram (0.006 mole) of potassium carbonate in 50 mL of methanol is stirred at ambient temperature for one hour. The reaction mixture is then concentrated under reduced pressure to a residue. The residue is taken up in about 75 mL of water, and the solution is extracted with two 200 mL portions of ethyl acetate. The combined extracts are dried with magnesium sulfate and filtered. The filtrate is concentrated under reduced pressure, yielding 2-amino-3-cyano-5-ethynylpyrazine. This reaction is repeated several times.

Step C Synthesis of 2-amino-3-cyano-5-[(4-trifluoromethylphenyl)ethynyl]pyrazine as an intermediate A solution of 3.2 grams (0.022 mole) of 2-amino-3-cyano-5-ethynylpyrazine, 8.4 grams (0.031 mole) of 4-trifluoromethylphenyl iodide, 10.7 grams (0.077 mole) of triethylamine, 0.5 gram (catalyst) of bis(triphenylphosphine) palladium(II) chloride, and 0.5 gram (catalyst) of copper iodide in 100 mL of acetonitrile is stirred at ambient temperature for about 18 hours. After this time the reaction mixture is concentrated under reduced pressure to a residue. The residue is partitioned between ethyl acetate and aqueous 1N hydrochloric acid. The two-layered mixture is filtered to remove a solid. The aqueous layer and the organic layer are separated, and the aqueous layer is washed with ethyl acetate. The ethyl acetate wash is combined with the organic layer, and the combination is washed with an aqueous solution of 10% lithium chloride. The organic layer is dried with magnesium sulfate and filtered. The filtrate is concentrated under reduced pressure to a residue. The residue is triturated with methylene chloride and filtered. The filtrate is subjected to column chromatography on silica gel. Elution is accomplished using methanol/methylene chloride combinations. The product-containing fractions are combined and concentrated under reduced pressure, yielding 2-amino-3-cyano-5-[(4-trifluoromethylphenyl)ethynyl]pyrazine.

Step D Synthesis of 2,4-diamino-6-[1-chloro-2-(4-trifluoromethyl-phenyl)ethenyl]pteridine (Compound 112)

This compound is prepared in a manner analogous to that of Step C of Example 7, using 2.9 grams (0.009 mole) of 2-amino-3-cyano-5-[(4-trifluoromethylphenyl)ethynyl]pyrazine and 0.9 gram (0.009 mole) of chloroformamidine hydrochloride in 20 mL of diglyme, yielding 2,4-diamino-6-[1-chloro-2-(4-trifluoromethylphenyl)ethenyl]pteridine.

EXAMPLE 10

SYNTHESIS OF 2,4-DIAMINO-6-(4-FLUOROPHENYLCARBONYL)-8-DEAZAPTERIDINE (COMPOUND 199)

Step A Synthesis of 3-amino-2-cyano-6-iodopyridine as an intermediate

A stirred suspension of 12.0 grams (0.08 mole) of 3-amino-6-chloro2-cyanopyridine [prepared by the method of Colbry, Elslager, and Werbel; previously cited] and 26.9 grams (0.18 mole) of sodium iodide in 300 mL of n-butanone is heated at reflux for about 3 days. After this time, the reaction mixture is concentrated under reduced pressure to a residue. The residue is then stirred with about 50 mL of water. The resultant solid is collected by filtration and washed with water. The solid is dried, yielding 3-amino-2-cyano-6-iodopyridine.

Step B Synthesis of 3-amino-2-cyano-6-(4-fluorophenylcarbonyl)pyridine as an intermediate This compound is prepared in a manner analogous to that of Step A of Example 8, using 2.5 grams (0.010 mole) of 3-amino-2-cyano-6-iodopyridine, 6.4 grams (0.013 mole) of tetramethylammonium tetra(4-fluorophenyl)borate, and 0.1 gram (0.0005 mole) of palladium(II) acetate in 50 mL of N,N-dimethylformamide, yielding 3-amino-2-cyano-6-(4-fluorophenylcarbonyl)pyridine.

Step C Synthesis of 2,4-diamino-6-(4-fluorophenylcarbonyl)-8-deazapteridine (Compound 199)

This compound is prepared in a manner analogous to that of Step C of Example 7, using 2.2 9 grams (0.009 mole) of 3-amino-2-cyano-6-(4-fluorophenylcarbonyl)pyridine and 0.9 gram (0.009 mole) chloroformamidine hydrochloride in 20 mL of diglyme, yielding 2,4-diamino-6-(4-fluorophenylcarbonyl)-8-deazapteridine.

EXAMPLE 11

SYNTHESIS OF 2,4-DIAMINO-6-[1-CHLORO-2-(4-CHLOROPHENYL)ETHENYL]-8-DEAZAPTERIDINE (COMPOUND 122)

Step A Synthesis of 3-amino-2-cyano-6-(trimethylsilylethynyl)pyridine as an intermediate This compound is prepared in a manner analogous to that of Step A of Example 9, using 3.8 grams (0.015 mole) of 3-amino-2-cyano-6-iodopyridine (prepared in Step A of Example 10), 2.1 grams (0.021 mole) of trimethylsilylacetylene, 10.6 mL of triethylamine, 0.13 gram of copper iodide, and 0.29 gram of bis(triphenylphosphine) palladium(II) chloride in 50 mL of acetonitrile, yielding 3-amino-2-cyano-6-(trimethylsilylethynyl)pyridine.

Step B Synthesis of 3-amino-2-cyano-6-ethynylpyridine as an intermediate

This compound is prepared in a manner analogous to that of Step B of Example 9, using 1.3 grams (0.006 mole) of 3-amino-2-cyano-6-(trimethylsilylethynyl)pyridine and 0.9 gram (0.006 mole) of potassium carbonate in 50 mL of methanol, yielding 3-amino-2-cyano-6-ethynylpyridine. This reaction is repeated several times.

Step C Synthesis of 3-amino-2-cyano-5-[(4-chlorophenyl)ethynyl]pyridine as an intermediate This compound is prepared in a manner analogous to that of Step C of Example 9, using 3.1 grams (0.022 mole) of 3-amino-2-cyano-6-ethynylpyridine, 7.4 grams (0.031 mole) of 4-chlorophenyl iodide, 10.7 grams (0.077 mole) of triethylamine, 0.5 gram (catalyst) of bis(triphenylphosphine) palladium(II) chloride, and 0.5 gram (catalyst) of copper iodide in 100 mL of acetonitrile, yielding 3-amino-2-cyano-6-[(4-chlorophenyl)ethynyl]pyridine.

Step D Synthesis of 2,4-diamino-6-[1-chloro-2-(4-chlorophenyl)-ethenyl]-8-deazapteridine (Compound 122)

This compound is prepared in a manner analogous to that of Step C of Example 7, using 2.3 grams (0.009 mole) of 3-amino-2-cyano-6-[(4-chlorophenyl)ethynyl]pyridine and 0.9 gram (0.009 mole) of chloroformamidine hydrochloride in 20 mL of diglyme, yielding 2,4-diamino-6-[1-chloro-2-(4-chlorophenyl)ethenyl]-8-deazapteridine.

EXAMPLE 12

SYNTHESIS OF 2,4-DIAMINO-6-(2,3-DIHYDRO-2,2-DIMETHYL-3-BENZOFURANON-7-YL)PTERIDINE

(COMPOUND 231)

Step A Synthesis of 7-bromo-2,3-dihydro-2,2-dimethylbenzofuran as an intermediate Under a nitrogen atmosphere, 10.0 grams (0.061 mole) of 7-amino-2,3-dihydro-2,2-dimethylbenzofuran was stirred and cooled in an ice-water bath. To this was added 17.4 mL (0.153 mole) of aqueous 48% hydrobromic acid, followed by the dropwise addition of a solution of 4.2 grams (0.061 mole) of sodium nitrite in 50 mL of water. The reaction mixture temperature was maintained at below 10° C. throughout the addition. In a separate reaction vessel, a stirred mixture of 4.8 grams (0.034 mole) of copper(I) bromide and 4.2 mL (0.037 mole) of aqueous 48% hydrobromic acid was heated to 60°–70° C., and the diazonium salt prepared above was added slowly dropwise. Upon completion of addition, the reaction mixture was warmed to 80° C. where it was stirred for one hour. After this time the reaction mixture was allowed to cool to ambient temperature as it stirred for about 18 hours. The reaction mixture was poured into 300 mL of water and the mixture was extracted with two 200 mL portions of diethyl ether. The combined extracts were dried with magnesium sulfate and filtered. The filtrate was concentrated under reduced pressure to a residual oil. The oil was subjected to column chromatography on silica gel. Elution was accomplished using petroleum ether. The product-containing fractions were combined and concentrated under reduced pressure, yielding 7.0 grams of 7-bromo-2,3-dihydro-2,2-dimethylbenzofuran. The NMR spectrum was consistent with the proposed structure.

Note: This compound was prepared in a manner disclosed by J. L. Hartwell (Org. Syn., Coll. Vol. III, Pg 185)

Step B Synthesis of 3,7-dibromo-2,3-dihydro-2,2-dimethylbenzofuran as an intermediate A stirring mixture of 7.0 grams (0.031 mole) of 7-bromo-2,3-dihydro-2,2-dimethylbenzofuran and 5.5 grams (0.031 mole) of N-bromosuccinimide in 150 mL of carbon tetrachloride is heated to reflux while irradiating with a sun lamp. The refluxing reaction mixture is stirred for about three hours, then it is cooled to ambient temperature. After this time the reaction mixture is washed with two 50 mL portions of aqueous 5% sodium bicarbonate solution, and one 50 mL portion of water. The organic layer is dried with magnesium sulfate and filtered. The filtrate is concentrated under reduced pressure, yielding 3,7-dibromo-2,3-dihydro-2,2-dimethylbenzofuran.

Step C Synthesis of 3-acetoxy-7-bromo-2,3-dihydro-2,2-dimethylbenzofuran as an intermediate A mixture of 7.6 grams (0.025 mole) of 3,7-dibromo-2,3-dihydro-2,2-dimethylbenzofuran and 11.3 grams (0.115 mole) of powdered potassium acetate in 125 mL of dry N,N-dimethylformamide is stirred at ambient temperature for about 24 hours. After this time, the reaction mixture is concentrated under reduced pressure to a residue. The residue is poured into about 350 mL of water and the mixture is extracted with diethyl ether. The ether extract is concentrated under reduced pressure, yielding 3-acetoxy-7-bromo-2,3-dihydro-2,2-dimethylbenzofuran.

Step D Synthesis of 2,3-dihydro-3-hydroxy-2,2-dimethylbenzofuran-7-ylboronic acid as an intermediate A stirring solution of 5.7 grams (0.020 mole) of 3-acetoxy-7-bromo-2,3-dihydro-2,2-dimethylbenzofuran in 150 mL of tetrahydrofuran is cooled to −80° C., and 18.2 mL of n-butyllithium in hexanes (2.5 Molar—0.046 mole) is added dropwise during a 15 minute period, while maintaining the reaction mixture temperature at about −80° C. Upon completion of the addition, the reaction mixture is stirred at −80° C. for 15 minutes. After this time, 6.9 mL (0.061 mole) of trimethyl borate is added during a 1 minute period. The reaction mixture is then allowed to warm slowly to ambient temperature during a 3 hour period, where it is stirred for an additional 1 hour. After this time, the reaction mixture is concentrated under reduced pressure to a volume of about 50 mL. The concentrate is then poured into 500 mL of icewater. The mixture is then made acidic with about 26 mL of aqueous 2N hydrochloric acid. The mixture is filtered, yielding 2,3-dihydro-3-hydroxy2,2-dimethylbenzofuran-7-ylboronic acid.

Note: This compound may be prepared in a manner disclosed by Thompson and Gaudino [JOC., 49, 5237–5243 (1984)]

Step E Synthesis of 2-amino-3-cyano-5-(2,3-dihydro-3-hydroxy-2,2-dimethylbenzofuran-7-yl)pyrazine as an intermediate This compound is prepared in a manner analogous to that of Step A of Example 4, using 1.6 grams (0.008 mole) of 2-amino-3-cyano-5-bromopyrazine, 2.5 grams (0.012 mole) of 2,3-dihydro-3-hydroxy-2,2-dimethyl-benzofuran-7-ylboronic acid, 4.3 grams (0.031 mole) of potassium carbonate and 0.3 gram of tetrakis(triphenylphosphine) palladium(0) in 150 mL of toluene, yielding 2-amino-3-cyano-5-(2,3-dihydro-3-hydroxy-2,2-dimethylbenzofuran-7-yl)pyrazine.

Step F Synthesis of 2,4-diamino-6-(2,3-dihydro-3-hydroxy-2,2-dimethylbenzofuran-7-yl)pteridine as an intermediate A solution of 2.8 grams (0.052 mole) of sodium methoxide in 100 mL of methanol is stirred, and 1.9 grams (0.019 mole) of guanidine hydrochloride is added. Upon completion of addition, the reaction mixture is stirred for about 5 minutes and then is filtered to remove sodium chloride. The filtrate is then added to 4.5 grams (0.016 mole) of 2-amino-3-cyano-5-(2,3-dihydro-3-hydroxy-2,2-dimethylbenzofuran-7-yl)pyrazine. The stirring reaction mixture is then heated to reflux where it is stirred for about 18 hours. After this time the reaction mixture is cooled and filtered. The filter cake is washed with water and dried, yielding 2,4-diamino-6-(2,3-dihydro-3-hydroxy-2,2-dimethylbenzofuran-7-yl)pteridine.

Note: This compound may be prepared in a manner disclosed by E. C. Taylor et al., [JACS., 95, 6413 (1973)]

Step G Synthesis of 2,4-diamino-6-(2,3-dihydro-2,2-dimethyl-3-benzofuranon-7-yl)pteridine (Compound 231)

A stirring solution of 1.8 grams (0.011 mole) of pyridine-sulfur trioxide complex [prepared by the method of E. E. Gilbert, Chem. Rev., 62. 551–555 (1962)] in 25 mL of methylene chloride is cooled to −60° C., and a solution of 2.0 grams (0.024 mole) of dimethyl sulfoxide in 5 mL of methylene chloride is added dropwise during a 5 minute period. Upon completion of addition, the reaction mixture is stirred at −60° C. for about 10 minutes. After this time a solution of 3.2 grams (0.10 mole) of 2,4-diamino-6-(2,3-dihydro-3-hydroxy-2,2-dimethylbenzofuran-7-yl)pteridine in 10 mL of methylene chloride is added dropwise during a 5 minute period. Upon completion of addition, the reaction mixture is again stirred at −60° C. for about 10 minutes, and then 5.1 grams (0.050 mole) of triethylamine is added dropwise during a 5 minute period. The reaction mixture is then allowed to warm to ambient temperature. After this time 30 mL of water is added, and the mixture is stirred for about 10 minutes. The aqueous layer is separated and extracted with about 20 mL of methylene chloride. The extract is combined with the organic layer, and the combination is concentrated under reduced pressure, yielding 2,4-diamino-6-(2,3-dihydro-2,2-dimethyl-3-benzofuranon-7-yl)pteridine.

Note: This compound may be prepared in a manner disclosed by D. Swern et al., Tetrahedron, 34, 1651–1660 (1978)

TABLE 1

2,4-DIAMINOPTERIDINES AND 8-DEAZAPTERIDINES AS INSECTICIDES

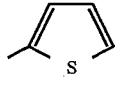

(I)

Where R and $R^1$ are amino; Q is nitrogen; and $R^3$ is -(n)$_m$-$R^4$

| Cmpd. No. | $R^2$ | m | n | $R^4$ |
|---|---|---|---|---|
| 1 | H | 1 | —CH$_2$CH$_2$— | 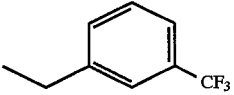 (thiophene) |
| 2 | —CH$_3$ | 0 | — | —CH$_3$ |
| 3 | —CH$_3$ | 1 | —S— | —CH$_3$ |
| 4 | —CH$_3$ | 1 | —C(=O)— | —CH$_3$ |
| 5 | 3-ethyl-CF$_3$-phenyl | 0 | — | H |

Where R and $R^1$ are amino; $R^2$ is hydrogen; Q is nitrogen; $R^3$ is -(n)$_m$-$R^4$, and $R^4$ is

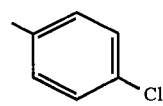

| Cmpd. No. | m | n | V | W | X | Y | Z |
|---|---|---|---|---|---|---|---|
| 6 | 0 | — | H | H | H | H | H |
| 7 | 0 | — | Cl | H | H | H | H |
| 8 | 0 | — | Cl | Cl | H | H | H |
| 9 | 0 | — | H | Cl | H | Cl | H |
| 10 | 0 | — | F | H | F | H | H |
| 11 | 0 | — | F | H | F | H | F |
| 12 | 0 | — | —CF$_3$ | H | H | H | H |
| 13 | 0 | — | H | —CF$_3$ | H | —CF$_3$ | H |
| 14 | 0 | — | —CN | H | H | H | H |
| 15 | 0 | — | —CO$_2$CH$_3$ | H | H | H | H |
| 16 | 0 | — | —OC(CH$_3$)$_2$CH$_2$— | H | H | H | |
| 17 | 0 | — | —OC(CH$_3$)$_2$CH$_2$— | H | Cl | H | |
| 18 | 0 | — | —CH$_2$C(CH$_3$)$_2$O— | H | H | H | |
| 19 | 0 | — | —OCF$_2$CF$_2$— | H | H | H | |
| 20 | 0 | — | —CF$_2$CF$_2$O— | H | H | H | |
| 21 | 0 | — | 4-Cl-phenyl | H | H | H | H |

TABLE 1-continued 2,4-DIAMINOPTERIDINES AND 8-DEAZAPTERIDINES AS INSECTICIDES

| | | | | | | | |
|---|---|---|---|---|---|---|---|
| 22 | 0 | — | 4-F-phenyl | H | H | H | H |
| 23 | 0 | — | 4-CF$_3$-phenyl | H | H | H | H |
| 24 | 0 | — | —CH$_3$ | phenyl | H | H | H |
| 25 | 1 | —CH$_2$CH$_2$— | H | H | H | H | H |
| 26 | 1 | —CH$_2$CH$_2$— | H | H | CF$_3$ | H | H |
| 27 | 1 | —CH$_2$CH$_2$— | —OCH$_3$ | H | H | —OCH$_3$ | H |
| 28 | 1 | —CH$_2$CH$_2$— | —OCH$_3$ | H | —OCH$_3$ | —OCH$_3$ | H |
| 29 | 1 | —CH$_2$NH— | H | H | Footnote[(1)] | H | H |
| 30 | 1 | —CH$_2$N(CH$_3$)— | H | H | Footnote[(1)] | H | H |

Where R and R$^1$ are amino; R$^2$ is methyl; Q is nitrogen; R$^3$ is -(n)$_m$-R$^4$, and R$^4$ is

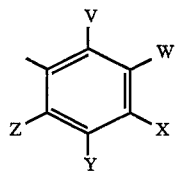

| Cmpd. No. | m | n | V | W | X | Y | Z |
|---|---|---|---|---|---|---|---|
| 31 | 0 | — | H | H | H | H | H |
| 32 | 0 | — | H | Cl | H | H | H |
| 33 | 0 | — | H | H | F | H | H |
| 34 | 0 | — | H | Cl | Cl | H | H |
| 35 | 0 | — | H | F | H | F | H |
| 36 | 0 | — | H | —CF$_3$ | H | H | H |
| 37 | 0 | — | H | —CF$_3$ | H | —CF$_3$ | H |
| 38 | 0 | — | H | —CN | H | H | H |
| 39 | 0 | — | H | —CO$_2$CH$_3$ | H | H | H |
| 40 | 0 | — | H | 4-Cl-phenyl | H | H | H |
| 41 | 0 | — | H | 4-F-phenyl | H | H | H |
| 42 | 0 | — | H | 4-CF$_3$-phenyl | H | H | H |
| 43 | 1 | —S— | H | H | Cl | H | H |

Where R, R$^1$, R$^2$ are amino; Q is nitrogen; and R$^3$ is -(n)$_m$-R$^4$

| Cmpd. No. | m | n | R$^4$ |
|---|---|---|---|
| 44 | 1 | —S— | —CH$_3$ |
| 45 | 1 | —S(O)$_2$— | —CH$_3$ |

TABLE 1-continued 2,4-DIAMINOPTERIDINES AND 8-DEAZAPTERIDINES AS INSECTICIDES

| 46 | 0 | — | 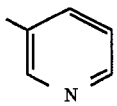 | | |

Where R, R¹, and R² are amino; Q is nitrogen; R³ is -(n)$_m$-R⁴, and R⁴ is

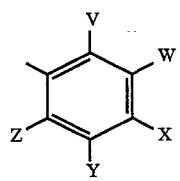

| Cmpd. No. | m | n | V | W | X | Y | Z |
|---|---|---|---|---|---|---|---|
| 47 | 0 | — | H | H | H | H | H |
| 48 | 0 | — | Cl | H | H | H | H |
| 49 | 0 | — | H | Cl | H | H | H |
| 50 | 0 | — | H | H | Cl | H | H |
| 51 | 0 | — | H | H | F | H | H |
| 52 | 0 | — | H | Cl | Cl | H | H |
| 53 | 0 | — | —CH₃ | H | H | H | H |
| 54 | 0 | — | H | —CF₃ | H | H | H |
| 55 | 0 | — | —CH=CHCH=CH— | | H | H | H |
| 56 | 0 | — | H | —CH=CHCH=CH— | | H | H |
| 57 | 0 | — | H | H | —O—C₆H₅ | H | H |
| 58 | 1 | —O— | H | H | H | H | H |
| 59 | 1 | —S— | H | H | H | H | H |
| 60 | 1 | —S— | H | H | Cl | H | H |
| 61 | 1 | —S— | H | H | Br | H | H |
| 62 | 1 | —S— | H | H | F | H | H |
| 63 | 1 | —S— | H | H | —C(CH₃)₃ | H | H |
| 64 | 1 | —S(O)₂— | H | H | H | H | H |

Where R, R¹, and R² are —N=CHN(CH₃)₂; Q is nitrogen, R³ is -(n)$_m$-R⁴; m is 0, and R⁴ is

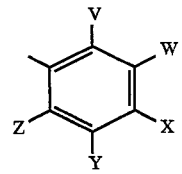

| Cmpd. No. | V | W | X | Y | Z |
|---|---|---|---|---|---|
| 65 | H | H | H | H | H |
| 66 | Cl | H | H | H | H |
| 67 | H | Cl | H | H | H |
| 68 | H | H | Cl | H | H |
| 69 | —CH=CHCH=CH— | | H | H | H |
| 70 | H | —CH=CHCH=CH— | | H | H |

Where R is amino; R³ is -(n)$_m$-R⁴, m is 0; and Q is nitrogen

| Cmpd. No. | R¹ | R² | R⁴ |
|---|---|---|---|
| 71 | —N(CH₃)₂ | —CH₃ | —CH₃ |
| 72 | —NH₂ | —CH(CH₃)₂ | —CH(CH₃)₂ |

TABLE 1-continued 2,4-DIAMINOPTERIDINES AND 8-DEAZAPTERIDINES AS INSECTICIDES

Where R and $R^1$ are amino; Q is nitrogen, $R^3$ is $-(n)_m-R^4$, and $R^4$ is

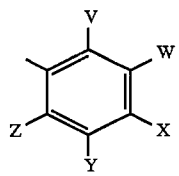

| Cmpd. No. | m | n | V | W | X | Y | Z | $R^2$ |
|---|---|---|---|---|---|---|---|---|
| 73 | 1 | —S— | H | H | Cl | H | H | —OH |
| 74 | 0 | — | H | H | H | H | H | phenyl |
| 75 | 1 | $\underset{C}{\overset{O}{\parallel}}$ | H | H | H | H | H | phenyl |

Where R and $R^1$ are amino; $R^2$ is hydrogen; Q is CH; and $R^3$ is $-(n)_m-R^4$, m is 0, and $R^4$ is

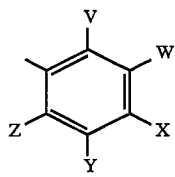

| Cmpd. No. | V | W | X | Y | Z |
|---|---|---|---|---|---|
| 76 | H | H | H | H | H |
| 77 | Cl | H | H | H | H |
| 78 | Cl | Cl | H | H | H |
| 79 | H | Cl | H | Cl | H |
| 80 | F | H | F | H | H |
| 81 | F | H | F | H | F |
| 82 | —$CF_3$ | H | H | H | H |
| 83 | H | —$CF_3$ | H | —$CF_3$ | H |
| 84 | —CN | H | H | H | H |
| 85 | —$CO_2CH_3$ | H | H | H | H |
| 86 | | —OC($CH_3$)$_2CH_2$— | H | H | H |
| 87 | | —OC($CH_3$)$_2CH_2$— | H | Cl | H |
| 88 | | —$CH_2$C($CH_3$)$_2$O— | H | H | H |
| 89 | | —$OCF_2CF_2$— | H | H | H |
| 90 | | —$CF_2CF_2$O— | H | H | H |
| 91 | 4-Cl-phenyl | H | H | H | H |
| 92 | 4-F-phenyl | H | H | H | H |
| 93 | 4-$CF_3$-phenyl | H | H | H | H |
| 94 | —$CH_3$ | phenyl | H | H | H |

TABLE 1-continued

2,4-DIAMINOPTERIDINES AND 8-DEAZAPTERIDINES AS INSECTICIDES

Where R and R$^1$ are amino; R$^2$ is methyl; Q is CH; R$^3$ is -(n)$_m$-R$^4$, m is 0, and R$^4$ is

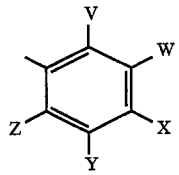

| Cmpd. No. | V | W | X | Y | Z |
|---|---|---|---|---|---|
| 95 | H | H | H | H | H |
| 96 | H | Cl | H | H | H |
| 97 | H | H | F | H | H |
| 98 | H | Cl | H | Cl | H |
| 99 | H | F | H | F | H |
| 100 | H | —CF$_3$ | H | H | H |
| 101 | H | —CF$_3$ | H | —CF$_3$ | H |
| 102 | H | —CN | H | H | H |
| 103 | H | —CO$_2$CH$_3$ | H | H | H |
| 104 | H | ⟨C$_6$H$_4$-Cl⟩ | H | H | H |
| 105 | H | ⟨C$_6$H$_4$-F⟩ | H | H | H |
| 106 | H | ⟨C$_6$H$_4$-CF$_3$⟩ | H | H | H |

Where R and R$^1$ are amino; m is 1, and R$^3$ is -(n)$_m$-R$^4$, where -(n)$_1$-R$^4$ is

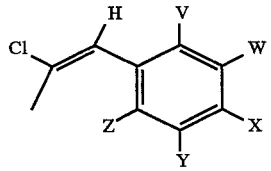

i.e., where n is haloalkenylene,

| Cmpd. No. | R$^2$ | Q | V | W | X | Y | Z |
|---|---|---|---|---|---|---|---|
| 107 | H | N | H | H | H | H | H |
| 108 | H | N | H | H | Cl | H | H |
| 109 | H | N | H | H | F | H | H |
| 110 | H | N | H | F | H | F | H |
| 111 | H | N | H | —CF$_3$ | H | H | H |
| 112 | H | N | H | H | —CF$_3$ | H | H |
| 113 | H | N | H | —CF$_3$ | H | —CF$_3$ | H |
| 114 | —CH$_3$ | N | H | H | H | H | H |
| 115 | —CH$_3$ | N | H | H | Cl | H | H |
| 116 | —CH$_3$ | N | H | H | F | H | H |
| 117 | —CH$_3$ | N | H | F | H | F | H |
| 118 | —CH$_3$ | N | H | —CF$_3$ | H | H | H |
| 119 | —CH$_3$ | N | H | H | —CF$_3$ | H | H |
| 120 | —CH$_3$ | N | H | —CF$_3$ | H | —CF$_3$ | H |
| 121 | H | CH | H | H | H | H | H |
| 122 | H | CH | H | H | Cl | H | H |
| 123 | H | CH | H | H | F | H | H |
| 124 | H | CH | H | F | H | F | H |
| 125 | H | CH | H | —CF$_3$ | H | H | H |

TABLE 1-continued 2,4-DIAMINOPTERIDINES AND 8-DEAZAPTERIDINES AS INSECTICIDES

| | | | | | | | |
|---|---|---|---|---|---|---|---|
| 126 | H | CH | H | H | −CF₃ | H | H |
| 127 | H | CH | H | −CF₃ | H | −CF₃ | H |
| 128 | −CH₃ | CH | H | H | H | H | H |
| 129 | −CH₃ | CH | H | H | Cl | H | H |
| 130 | −CH₃ | CH | H | H | F | H | H |
| 131 | −CH₃ | CH | H | F | H | F | H |
| 132 | −CH₃ | CH | H | −CF₃ | H | H | H |
| 133 | −CH₃ | CH | H | H | −CF₃ | H | H |
| 134 | −CH₃ | CH | H | −CF₃ | H | −CF₃ | H |

Where R and R¹ are amino; m is 1, and R³ is -(n)ₘ-R⁴,
where -(n)₁-R⁴ is

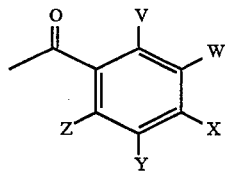

i.e., where n is carbonyl,

| Cmpd. No. | R² | Q | V | W | X | Y | Z |
|---|---|---|---|---|---|---|---|
| 135 | H | N | H | H | H | H | H |
| 136 | H | N | Cl | H | H | H | H |
| 137 | H | N | H | Cl | H | H | H |
| 138 | H | N | H | Cl | Cl | H | H |
| 139 | H | N | H | H | Cl | H | H |
| 140 | H | N | −CF₃ | H | H | H | H |
| 141 | H | N | H | −CF₃ | H | H | H |
| 142 | H | N | H | −CF₃ | H | −CF₃ | H |
| 143 | H | N | H | H | −CF₃ | H | H |
| 144 | H | N | H | −CO₂CH₃ | H | H | H |
| 145 | H | N | F | H | H | H | H |
| 146 | H | N | H | H | −CO₂CH₃ | H | H |
| 147 | H | N | H | F | H | H | H |
| 148 | H | N | H | −CN | H | H | H |
| 149 | H | N | H | F | H | F | H |
| 150 | H | N | H | H | −CN | H | H |
| 151 | H | N | H | H | F | H | H |
| 152 | H | N | F | H | F | H | F |
| 153 | H | N | H | -C₆H₄-F (4-) | H | H | H |
| 154 | H | N | H | -C₆H₄-Cl (4-) | H | H | H |
| 155 | H | N | H | -C₆H₄-CF₃ (4-) | H | H | H |
| 156 | H | N | H | H | -C₆H₄-F (4-) | H | H |
| 157 | H | N | H | H | -C₆H₄-Cl (4-) | H | H |
| 158 | H | N | H | H | -C₆H₄-CF₃ (4-) | H | H |

TABLE 1-continued 2,4-DIAMINOPTERIDINES AND 8-DEAZAPTERIDINES AS INSECTICIDES

| # | | | | | | | |
|---|---|---|---|---|---|---|---|
| 159 | —CH₃ | N | H | H | H | H | H |
| 160 | —CH₃ | N | Cl | H | H | H | H |
| 161 | —CH₃ | N | H | Cl | H | H | H |
| 162 | —CH₃ | N | H | Cl | Cl | H | H |
| 163 | —CH₃ | N | H | H | Cl | H | H |
| 164 | —CH₃ | N | —CF₃ | H | H | H | H |
| 165 | —CH₃ | N | H | —CF₃ | H | H | H |
| 166 | —CH₃ | N | H | —CF₃ | H | —CF₃ | H |
| 167 | —CH₃ | N | H | H | —CF₃ | H | H |
| 168 | —CH₃ | N | H | —CO₂CH₃ | H | H | H |
| 169 | —CH₃ | N | F | H | H | H | H |
| 170 | —CH₃ | N | H | H | —CO₂CH₃ | H | H |
| 171 | —CH₃ | N | H | F | H | H | H |
| 172 | —CH₃ | N | H | —CN | H | H | H |
| 173 | —CH₃ | N | H | F | H | F | H |
| 174 | —CH₃ | N | H | H | —CN | H | H |
| 175 | —CH₃ | N | H | H | F | H | H |
| 176 | —CH₃ | N | F | H | F | H | F |
| 177 | —CH₃ | N | H | 4-F-C₆H₄— | H | H | H |
| 178 | —CH₃ | N | H | 4-Cl-C₆H₄— | H | H | H |
| 179 | —CH₃ | N | H | 4-CF₃-C₆H₄— | H | H | H |
| 180 | —CH₃ | N | H | H | 4-F-C₆H₄— | H | H |
| 181 | —CH₃ | N | H | H | 4-Cl-C₆H₄— | H | H |
| 182 | —CH₃ | N | H | H | 4-CF₃-C₆H₄— | H | H |
| 183 | H | CH | H | H | H | H | H |
| 184 | H | CH | Cl | H | H | H | H |
| 185 | H | CH | H | Cl | H | H | H |
| 186 | H | CH | H | Cl | Cl | H | H |
| 187 | H | CH | H | H | Cl | H | H |
| 188 | H | CH | —CF₃ | H | H | H | H |
| 189 | H | CH | H | —CF₃ | H | H | H |
| 190 | H | CH | H | —CF₃ | H | —CF₃ | H |
| 191 | H | CH | H | H | —CF₃ | H | H |
| 192 | H | CH | H | —CO₂CH₃ | H | H | H |
| 193 | H | CH | F | H | H | H | H |
| 194 | H | CH | H | H | —CO₂CH₃ | H | H |
| 195 | H | CH | H | F | H | H | H |
| 196 | H | CH | H | —CN | H | H | H |
| 197 | H | CH | H | F | H | F | H |
| 198 | H | CH | H | H | —CN | H | H |
| 199 | H | CH | H | H | F | H | H |
| 200 | H | CH | F | H | F | H | F |
| 201 | H | CH | H | 4-F-C₆H₄— | H | H | H |

TABLE 1-continued

2,4-DIAMINOPTERIDINES AND 8-DEAZAPTERIDINES AS INSECTICIDES

| | | | | | | | |
|---|---|---|---|---|---|---|---|
| 202 | H | CH | H | 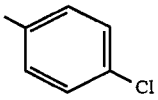 4-Cl-C6H4 | H | H | H |
| 203 | H | CH | H | 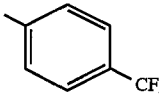 4-CF3-C6H4 | H | H | H |
| 204 | H | CH | H | H | 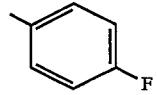 4-F-C6H4 | H | H |
| 205 | H | CH | H | H | 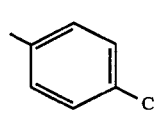 4-Cl-C6H4 | H | H |
| 206 | H | CH | H | H | 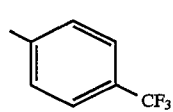 4-CF3-C6H4 | H | H |
| 207 | —CH3 | CH | H | H | H | H | H |
| 208 | —CH3 | CH | Cl | H | H | H | H |
| 209 | —CH3 | CH | H | Cl | H | H | H |
| 210 | —CH3 | CH | H | Cl | Cl | H | H |
| 211 | —CH3 | CH | H | H | Cl | H | H |
| 212 | —CH3 | CH | —CF3 | H | H | H | H |
| 213 | —CH3 | CH | H | —CF3 | H | H | H |
| 214 | —CH3 | CH | H | —CF3 | H | —CF3 | H |
| 215 | —CH3 | CH | H | H | —CF3 | H | H |
| 216 | —CH3 | CH | H | —CO2CH3 | H | H | H |
| 217 | —CH3 | CH | F | H | H | H | H |
| 218 | —CH3 | CH | H | H | —CO2CH3 | H | H |
| 219 | —CH3 | CH | H | F | H | H | H |
| 220 | —CH3 | CH | H | —CN | H | H | H |
| 221 | —CH3 | CH | H | F | H | F | H |
| 222 | —CH3 | CH | H | H | —CN | H | H |
| 223 | —CH3 | CH | H | H | F | H | H |
| 224 | —CH3 | CH | F | H | F | H | F |
| 225 | —CH3 | CH | H | 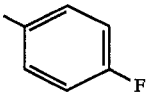 4-F-C6H4 | H | H | H |
| 226 | —CH3 | CH | H | 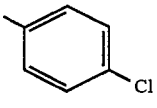 4-Cl-C6H4 | H | H | H |
| 227 | —CH3 | CH | H | 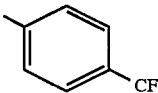 4-CF3-C6H4 | H | H | H |
| 228 | —CH3 | CH | H | H | 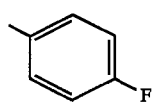 4-F-C6H4 | H | H |
| 229 | —CH3 | CH | H | H | 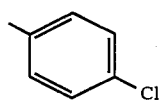 4-Cl-C6H4 | H | H |

TABLE 1-continued

2,4-DIAMINOPTERIDINES AND 8-DEAZAPTERIDINES AS INSECTICIDES

| 230 | —CH₃ | CH | H | H | 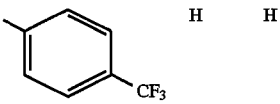 | H | H |

Where R and R¹ are amino; R² is hydrogen; Q is nitrogen; R³ is -(n)$_m$-R⁴, and R⁴ is

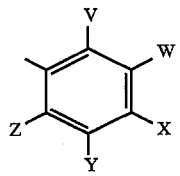

| Cmpd. No. | m | n | V | W | X | Y | Z |
|---|---|---|---|---|---|---|---|
| 231 | 0 | — | | —OC(CH₃)₂C(=O)— | H | H | H |
| 232 | 0 | — | | —OC(CH₃)₂C(=O)— | H | Cl | H |
| 233 | 0 | — | | —(C=O)C(CH₃)₂O— | H | H | H |
| 234 | 0 | — | | —(C=O)C(CH₃)₂O— | H | Cl | H |

(1) X in Compounds 29 and 30 is —C(=O)NHCH(CO₂H)CH₂CH₂CO₂H

Insecticide Formulations

In the normal use of the insecticidal pteridines of the present invention, they usually will not be employed free from admixture or dilution, but ordinarily will be used in a suitable formulated composition compatible with the method of application and comprising an insecticidally effective amount of the pteridines. The pteridines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present pteridines may be applied, for example, as sprays, dusts, or granules to the area where pest control is desired, the type of application varying of course with the pest and the environment. Thus, the pteridines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these pteridines compounds.

Granules may comprise porous or nonporous particles, such as attapulgite clay or sand, for example, which serve as carriers for the pteridines. The granule particles are relatively large, a diameter of about 400–2500 microns typically. The particles are either impregnated with the pteridine from solution or coated with the pteridine, adhesive sometimes being employed. Granules generally contain 0.05–10%, preferably 0.5–5%, active ingredient as the insecticidally effective amount.

Dusts are admixtures of the prteridines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which acts carriers for the insecticide.

These finely divided solids have an average particle size of less than about 50 microns. A typical dust formulation useful for controlling insects contains 1 part of 2,4-diamino-6-[3,5-di(trifluoromethyl)phenyl]-7-methylpteridine (Compound 37) and 99 parts of talc.

The pteridines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% pteridine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, Compound 37 is formulated as a 10% wettable powder (10% WP) as follows:

| COMPONENT | AMOUNT (wt/wt) |
|---|---|
| Compound 37 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the pteridines with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethyl sulfoxide solutions incorporated into an artificial insect diet. Alternatively, they could be used as aqueous acetone or methanol solutions containing a small amount of octylphenoxypolyethoxyethanol surfactant for use as foliar sprays. An insecticidally effective amount of pteridine in an insecticidal composition diluted for application is normally in the range of about 0.001% to about 8% by weight. Many variations of spraying and dusting compositions known in the art may be used by substituting the pteridine of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of pteridine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

The pteridines of the present invention were incorporated into an artificial diet for evaluation of insecticidal activity against the tobacco budworm (*Heliothis virescens* [Fabricius]).

Stock solutions of test chemical in dimethyl sulfoxide were prepared for each rate of application. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.) wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control.

Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. Where possible, the negative log of the concentration of the test chemical that provided 50% mortality ($pLC_{50}$) was also determined.

The compounds of the present invention were tested in the diet test as insect growth inhibitors against the larvae of tobacco budworm (above). The results of this testing are set forth in Table 2 below.

In this test it will be seen that many of the compounds of this invention, including Compounds 3, 26, 34, 36, 47, 48, 52, 53, 60, 62, 72, and 74 all had $pI_{50}$ values of 4.0 or higher, i.e. they were highly active as inhibitors of the growth of tobacco budworm larvae.

TABLE 2

Insecticidal Activity of 2,4-Diamino-6-phenylpteridines and 8-Deazapteridines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
| --- | --- | --- | --- | --- | --- |
| 1 | 6 | 7 | <4.0 | 0 | — |
|   | 5 | 17 |      | 0 |   |
|   | 4 | 40 |      | 0 |   |
| 3 | 8 | 22 | 4.1  | 0 | <4.0 |
|   | 7 | 28 |      | 0 |   |
|   | 6 | 22 |      | 0 |   |

TABLE 2-continued

Insecticidal Activity of 2,4-Diamino-6-phenylpteridines and 8-Deazapteridines Incorporated into the Diet of Tobacco Budworm

| Cmpd. No. | Rate of Application[1] | Percent Growth Inhibition[2,3,4] | $pI_{50}$[5] | Percent Mortality[6] | $pLC_{50}$[7] |
|---|---|---|---|---|---|
|  | 5 | 40 |  | 15 |  |
|  | 4 | 51 |  | 30 |  |
| 4 | 3 | 66 | ~3.0 | 0 | — |
| 5 | 4 | 21 | <4.0 | 0 | — |
| 25 | 5 | 4 | <4.0 | 0 | — |
|  | 4 | 26 |  | 0 |  |
| 26 | 6 | −1 | 4.6 | 0 | — |
|  | 5 | 30 |  | 0 |  |
|  | 4 | 72 |  | 0 |  |
| 27 | 5 | 8 | — | 0 | — |
|  | 4 | 3 |  | 0 |  |
| 28 | 5 | −3 | — | 0 | — |
|  | 4 | 20 |  | 0 |  |
| 34 | 5.0 | 3 | 4.2 | — |  |
|  | 4.5 | 37 |  | — |  |
|  | 4.0 | 69 |  | — |  |
|  | 3.5 | 87 |  | — |  |
|  | 3.0 | 99 |  | 65 | — |
| 36 | 5.0 | 8 | 4.2 | — |  |
|  | 4.5 | 28 |  | — |  |
|  | 4.0 | 59 |  | — |  |
|  | 3.5 | 93 |  | — |  |
|  | 3.0 | 99 |  | 10 | — |
| 43 | 3.0 | −9 | — | — | — |
| 44 | 5.0 | −31 | 3.6 | — |  |
|  | 4.5 | −33 |  | — |  |
|  | 4.0 | 18 |  | — |  |
|  | 3.5 | 54 |  | — |  |
|  | 3.0 | 94 |  | 40 | — |
| 45 | 5.0 | 10 | 3.9 | — |  |
|  | 4.5 | 19 |  | — |  |
|  | 4.0 | 43 |  | — |  |
|  | 3.5 | 68 |  | — |  |
|  | 3.0 | 96 |  | 30 | — |
| 47 | 5.0 | 29 | 4.3 | — |  |
|  | 4.5 | 38 |  | — |  |
|  | 4.0 | 53 |  | — |  |
|  | 3.5 | 76 |  | — |  |
|  | 3.0 | 97 |  | — | — |
| 48 | 5 | 21 | 4.0 | 0 | — |
|  | 4 | 51 |  | 15 |  |
| 49 | 6 | 3 | <4.0 | 0 | — |
|  | 5 | 36 |  | 0 |  |
|  | 4 | 26 |  | 0 |  |
| 50 | 4 | 22 | <4.0 | 0 | — |
| 51 | 4 | 25 | <4.0 | 0 | — |
| 52 | 5.0 | 12 | 4.0 | — |  |
|  | 4.5 | 34 |  | — |  |
|  | 4.0 | 59 |  | — |  |
|  | 3.5 | 67 |  | — |  |
|  | 3.0 | 81 |  | 10 | — |
| 53 | 5.0 | 43 | 4.3 | — | — |
|  | 4.5 | 37 |  | — |  |
|  | 4.0 | 64 |  | — |  |
|  | 3.5 | 79 |  | — |  |
|  | 3.0 | 91 |  | — |  |
| 54 | 5 | 4 | <4.0 | 0 | — |
|  | 4 | 32 |  | 0 |  |
| 55 | 6 | 8 | <4.0 | 0 | — |
|  | 5 | 19 |  | 0 |  |
|  | 4 | 36 |  | 10 |  |
| 56 | 4 | 20 | — | 0 | — |
| 57 | 4 | 38 | <4.0 | 0 | — |
| 58 | 5.0 | 24 | 3.8 | — | — |
|  | 4.5 | 16 |  | — |  |
|  | 4.0 | 40 |  | — |  |
|  | 3.5 | 61 |  | — |  |
|  | 3.0 | 96 |  | — |  |
| 59 | 5.0 | 12 | 3.7 | — | — |
|  | 4.5 | 9 |  | — |  |
|  | 4.0 | 26 |  | — |  |
|  | 3.5 | 64 |  | — |  |
|  | 3.0 | 82 |  | — |  |
| 60 | 5.0 | 14 | 4.2 | — | — |
|  | 4.5 | 37 |  | — |  |
|  | 4.0 | 56 |  | — |  |
|  | 3.5 | 85 |  | — |  |
|  | 3.0 | 91 |  | — |  |
| 61 | 3 | 60 | — | — | — |
| 62 | 5.0 | 30 | 4.3 | — |  |
|  | 4.5 | 37 |  | — |  |
|  | 4.0 | 66 |  | — |  |
|  | 3.5 | 95 |  | — |  |
|  | 3.0 | 100 |  | 100 | ~3.0 |
| 63 | 3 | 17 | — | — | — |
| 64 | 4 | −5 | — | 0 | — |
| 65 | 5.0 | 28 | 3.3 | — | — |
|  | 4.5 | 6 |  | — |  |
|  | 4.0 | −1 |  | — |  |
|  | 3.5 | 27 |  | — |  |
|  | 3.0 | 75 |  | — |  |
| 66 | 5.0 | 1 | ~3.7 | — | — |
|  | 4.5 | 61 |  | — |  |
|  | 4.0 | 43 |  | — |  |
|  | 3.5 | 64 |  | — |  |
|  | 3.0 | 70 |  | — |  |
| 67 | 5.0 | 24 | 3.3 | — | — |
|  | 4.5 | 21 |  | — |  |
|  | 4.0 | 15 |  | — |  |
|  | 3.5 | 33 |  | — |  |
|  | 3.0 | 67 |  | — |  |
| 68 | 5.0 | 16 | ~3.2 | — | — |
|  | 4.5 | −9 |  | — |  |
|  | 4.0 | 7 |  | — |  |
|  | 3.5 | 6 |  | — |  |
|  | 3.0 | 71 |  | — |  |
| 69 | 4 | 29 | <4.0 | 0 | — |
| 70 | 4 | −1 | — | 0 | — |
| 72 | 5.0 | 62 | >5.0 | — | — |
|  | 4.5 | 75 |  | — |  |
|  | 4.0 | 85 |  | — |  |
|  | 3.5 | 92 |  | — |  |
|  | 3.0 | 97 |  | — |  |
| 73 | 3 | −7 | — | — | — |
| 74 | 5.0 | 13 | 4.1 | — | — |
|  | 4.5 | 20 |  | — |  |
|  | 4.0 | 56 |  | — |  |
|  | 3.5 | 79 |  | — |  |
|  | 3.0 | 97 |  | — |  |
| 75 | 3 | 16 | — | — | — |

FOOTNOTES - TABLE 2
[1]The rate of application is expressed as the negative log of the molar concentration of the test compound in the diet.
[2]Percent growth inhibition is derived from the total weight of the insects (IW) at each rate of application in the test relative to the total weight of insects in an untreated control,
% Gr. Inh. = [IW(control) − IW(test)/IW(control)] × 100
[3]ND = No data
[4]A minus % growth inhibition indicates that the insects weighed more at the termination of the test than those in the untreated control.
[5]$pI_{50}$ is the negative log of the concentration of the test chemical that provides 50% growth inhibition in the test insects.
[6]Percent mortality is derived from the number of dead insects (TD) relative to the total number of insects (TI) used in the test,
% Mortality = $\frac{TD}{TI}$ × 100
[7]$pLC_{50}$ is the negative log of the concentration of the test chemical that provides 50% mortality of the test insects.

We claim:

1. An insecticidal composition comprising, in admixture with an agriculturally acceptable carrier and a surface-active agent, an insecticidally effective amount of a pteridine or 8-deazapteridine compound of the formula:

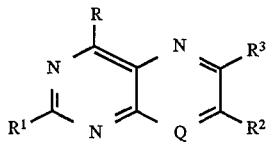
(I)

wherein

R and R¹ are independently selected from amino, lower alkylamino, di(lower alkyl)amino, or di(lower alkyl)aminomethyleneamino;

R² is hydrogen, amino, lower alkyl, di(lower alkyl)aminomethyleneamino, hydroxy, lower alkoxy, phenyl or substituted phenyl, haloalkylphenylalkyl;

Q is N or CH;

R³ is $-(n)_m-R^4$, where m is 0 or 1; wherein
when m is 1, n is a bridging atom or moiety selected from oxygen, sulfur, sulfinyl, sulfonyl, lower alkylene, lower alkenylene, lower alkynylene, lower haloalkenylene, carbonyl, aminomethyl, or (substituted amino)methyl; and R⁴ is hydrogen, lower alkyl, thien-2-yl, pyridin-3-yl, or

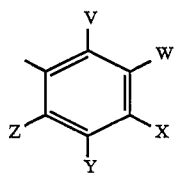

wherein

V, W, X, Y, and Z am independently selected from the group consisting of hydrogen, halogen, lower alkyl, lower alkoxy, lower haloalkyl, cyano, lower alkoxycarbonyl, aminocarbonyl, phenyl optionally substituted with chloro, fluoro, or trifluoromethyl; or phenoxy optionally substituted with chloro, fluoro, or trifluoromethyl; wherein optionally V and W taken together form a fused ring and are —OC(CH₃)₂CH₂—, —CH₂C(CH₃)₂O—, —OC(CH₃)₂C(=O)—, —C(=O)C(CH₃)₂O—, —OCF₂CF₂—, or —CF₂CF₂O—, to provide, respectively, the corresponding 2,3-dihydro-2,2-dimethylbenzofuran-7-yl, 2,3-dihydro-2,2-dimethylbenzofuran-4-yl, 2,3-dihydro-2,2-dimethyl-3-benzofuranon-7-yl, 2,3-dihydro-2,2-dimethyl-3-benzofuranon-4-yl, 2,2,3,3-tetrafluorobenzofuran-7-yl, and 2,2,3,3-tetrafluorobenzofuran-4-yl moieties; or, optionally, V and W or W and X taken together are —CH=CHCH=CH—, forming the corresponding naphth-1-yl and naphth-2-yl rings.

2. The composition of claim 1 wherein

R and R¹ are amino;
R² is hydrogen or lower alkyl;
Q is N or CH;
R³ is $-(n)_m-R^4$, where m is 0; and R⁴ is

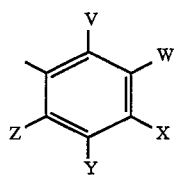

wherein

Z and X are independently selected from hydrogen and fluoro; and V, W, and Y are independently selected from hydrogen, halogen, lower haloalkyl, carboxy, lower alkoxycarbonyl, phenyl, and phenyl substituted with halogen or lower haloalkyl, phenoxy and phenoxy substituted with halogen or lower haloalkyl, V and W taken together form a fused ring and are —OC(CH₃)₂CH₂—, —CH₂C(CH₃)₂O—, —OC(CH₃)₂C(=O)—, —C(=O)C(CH₃)₂O—, with the proviso that at least one of V, W, or Y must be a substituent other than hydrogen.

3. The composition of claim 1 wherein

R and R¹ are amino;
R² is hydrogen or lower alkyl;
Q is N or CH;
R³ is $-(n)_m-R^4$, where m is 1, n is carbonyl or lower haloalkenylene, and R⁴ is

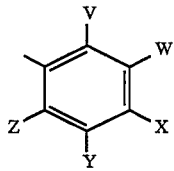

wherein

V, W, X, and Y are independently selected from hydrogen, halogen, lower haloalkyl, phenyl, phenyl substituted with halogen or lower haloalkyl, phenoxy, or phenoxy substituted with halogen or lower haloalkyl, and Z is hydrogen or halogen.

4. The composition of claim 1 wherein, when m is 0, V, X and Z are hydrogen, and W and Y are halogen or trifluoromethyl.

5. The composition of claim 1 wherein, when m is 0, W, X, Y, and Z are hydrogen, and V is 4-chlorophenyl.

6. The composition of claim 1 wherein, when m is 0, V, X, Y, and Z are hydrogen, and W is 4-fluorophenyl.

7. The composition of claim 1 wherein, when m is 0, X and Z are hydrogen, Y is hydrogen or chloro, and V and W taken together form a fused ring and are —OC(CH₃)₂CH₂—, —CH₂C(CH₃)₂O—, —OC(CH₃)₂C(=O) —, and —C(=O)C(CH₃)₂O—.

8. The composition of claim 1 wherein, when m is 1, and n is carbonyl, V, X, and Z are hydrogen, and W and Y are trifluoromethyl.

9. The composition of claim 1 wherein, when m is 1, and n is carbonyl, V, X, Y, and Z are hydrogen, and W is 4-trifluoromethylphenyl.

10. The composition of claim 1 wherein, when m is 1, and n is carbonyl, V, W, Y, and Z are hydrogen, and X is 4-fluorophenyl.

11. The composition of claim 1, wherein, when m is 1, and n is lower haloalkenylenyl, V, W, Y, and Z are hydrogen, and X is chloro or trifluoromethyl.

12. The composition of claim 1 wherein the pteridine compound is 2,4-diamino-6-(2-chlorophenylcarbonyl)pteridine.

13. The composition of claim 1 wherein R and $R^1$ are amino.

14. The composition of claim 1 wherein $R^2$ is hydrogen or lower alkyl.

15. The composition of claim 1 wherein Q is N.

16. The composition of claim 1 wherein
$R^3$ is $-(n)_m-R^4$, where m is 0; and
$R^4$ is

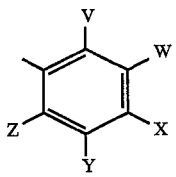

wherein
Z and X are independently selected from hydrogen and fluoro; and V, W, and Y are independently selected from hydrogen, halogen, lower haloalkyl, carboxy, lower alkoxycarbonyl, phenyl, phenyl substituted with halogen or lower alkyl, phenoxy, phenoxy substituted with halogen or lower haloalkyl; or V and W taken together form a fused ring and are —OC(CH$_3$)$_2$CH$_2$—, —CH$_2$C(CH$_3$)$_2$O—, —OC(CH$_3$)$_2$C(=O)—, or —C(=O)C(CH$_3$)$_2$O—, with the proviso that at least one of V, W, or Y must be a substituent other than hydrogen.

17. The composition of claim 1 wherein
$R^3$ is $-(n)_m-R^4$, where m is 1, n is carbonyl or lower haloalkenylene, and
$R^4$ is

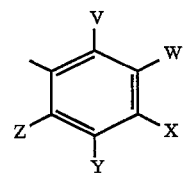

wherein
V, W, X, and Y are independently selected from hydrogen, halogen, lower haloalkyl, phenyl, phenyl substituted with halogen or lower haloalkyl, phenoxy, or phenoxy substituted with halogen or lower haloalkyl, and Z is hydrogen or halogen.

18. The composition of claim 1 wherein the surface-active agent is a wetting agent, a dispersing agent, an emulsifying agent, or mixtures thereof.

19. The composition of claim 1 wherein Q is CH.

* * * * *